United States Patent [19]
Muchel et al.

[11] 4,270,842
[45] Jun. 2, 1981

[54] OPTICAL SYSTEM FOR FORMING AN IMAGE OF THE RETINA

[75] Inventors: Franz Muchel, Königsbronn; Werner Böhning, Oberkochen, both of Fed. Rep. of Germany

[73] Assignee: Carl Zeiss Stiftung, Oberkochen, Fed. Rep. of Germany

[21] Appl. No.: 895,689

[22] Filed: Apr. 12, 1978

[30] Foreign Application Priority Data

Apr. 15, 1977 [DE] Fed. Rep. of Germany ....... 2716614

[51] Int. Cl.³ .................. G02B 3/08; A61B 3/10
[52] U.S. Cl. ........................ 350/452; 351/6; 351/16
[58] Field of Search ........... 350/179, 211, 189; 351/16, 6, 7

[56] References Cited

U.S. PATENT DOCUMENTS

| | | | |
|---|---|---|---|
| 3,944,341 | 3/1976 | Pomerantzeff | 350/179 X |
| 3,973,836 | 8/1976 | Govignon | 351/16 X |

FOREIGN PATENT DOCUMENTS

| | | | |
|---|---|---|---|
| 491207 | 2/1930 | Fed. Rep. of Germany | 350/211 |
| 1188326 | 3/1965 | Fed. Rep. of Germany | 351/6 |

OTHER PUBLICATIONS

Howard C. Howland, "Photorefraction . . . ", *JOSA*, vol. 64, No. 2, 2/74, pp. 240-249.
Robert N. Shaffer et al., "A Comparative . . . ", *Amer. J. Ophthalmology*, vol. 41, 2/56, pp. 256-264.

*Primary Examiner*—Paul A. Sacher
*Attorney, Agent, or Firm*—Stonebraker, Shepard & Stephens

[57] ABSTRACT

An optical system for forming an image of the retina of an eye which is to be examined. The optical system has two groups of lenses which cooperate to form the image. The first lens group is in contact with the cornea of the eye of the patient via the eye liquid or a physiological saline solution. The second lens group is separated from the first group by an air space, and may serve to conjugate the pupil of the patient with the pupil of the doctor or other observer. If desired, the lenses of the first group may have a central opening which receives a light pipe for illuminating the eye of the patient. Also, if desired, the lenses of the second group may include either spherical or aspherical lenses, or a combination of both, or may include one or more Fresnel lenses.

1 Claim, 2 Drawing Figures

OPTICAL SYSTEM FOR FORMING AN IMAGE OF THE RETINA

BACKGROUND OF THE INVENTION

The invention relates to an optical system for forming an image of the retina of an eye to be examined.

In order to form an image of the retina, it is already known to use contact lenses. The known systems have the disadvantage that they can form an image of only small areas of the retina, and that in order to examine the entire area of the retina, it is necessary to swing the optical system to form successive images of different regions of the retina, one after the other.

An object of the present invention is to provide an optical system which is able, from a single fixed position, to form an image of a relatively large area of the retina, approximately up to the "ora serrata."

This object is attained according to the invention by providing two lens groups which cooperate to form an image of a relatively large area of the retina. The first lens group is in substantial contact with the cornea of the eye of the patient, via the natural eye liquid or a physiological saline solution. The second lens group is spaced from the first lens group by an air space. The curvatures and refractive powers of the lenses are preferably so dimensioned that the image of the retina which is produced is flattened.

The second lens group can advantageously consist of Fresnel lenses. However, it is also possible to construct the second lens group from a combination of spherical or aspherical lenses with Fresnel lenses.

In one embodiment of the invention, an adapter for the attachment of reproduction apparatus (a camera or the like) or projection apparatus, is provided behind the second lens group.

The illumination of the fundus or retina can be effected in known manner with mono-light-transmitting fibers arranged in a ring around the imaging system. However, it is also possible to provide the first lens group with a central borehole which receives the end of a light pipe for illuminating the eye of the patient. Light is furnished to the opposite end of the light pipe from any convenient conventional illuminating means.

The advantages obtained with this invention include, in particular, the fact that the examining apparatus need not be swung or shifted from one position to another, in order to cover the entire retina. It provides an approximately 1.5 times enlargement of the fundus or retina which is being observed. In order to increase the enlargement of the image of the fundus, an ocular or a viewing lens system with documentation possibilities (e.g., a camera or other means for taking a picture) can be arranged in known manner behind the optical system.

DESCRIPTION OF THE PREFERRED EMBODIMENTS

Figure 1:
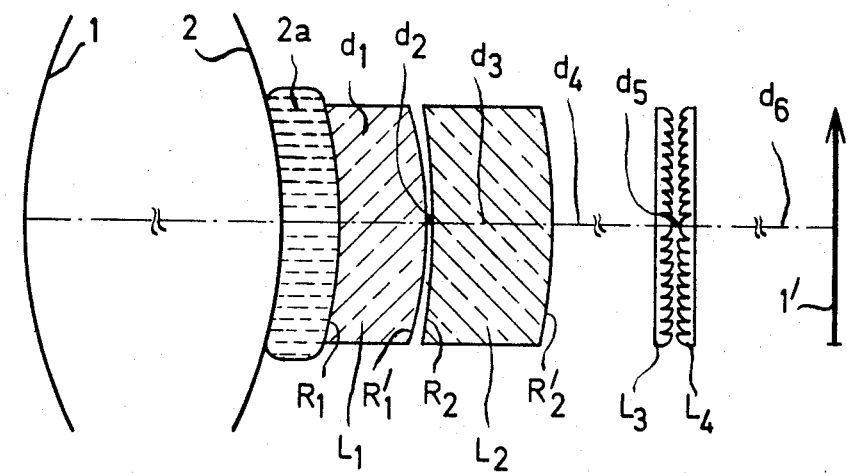
FIG. 1 is a schematic view in axial section through an optical system in accordance with one embodiment of the invention, without an illuminating device.

Referring now to FIG. 1, the fundus or retina of the eye of the patient to be examined is indicated schematically at 1, and the cornea of the eye at 2. The first lens group of the optical system is made up of the lenses $L_1$ and $L_2$, of which the first lens $L_1$ is substantially in contact with the cornea of the eye by means of an interposed body of liquid 2a, which may be either the natural eye liquid or a physiological saline solution.

The second lens group of the optical system of the present invention, in this first embodiment, is composed of the two Fresnel lenses $L_3$ and $L_4$. At 1' there is shown diagrammatically the flattened image of the fundus or retina 1, as formed by the lens system.

Figure 2:
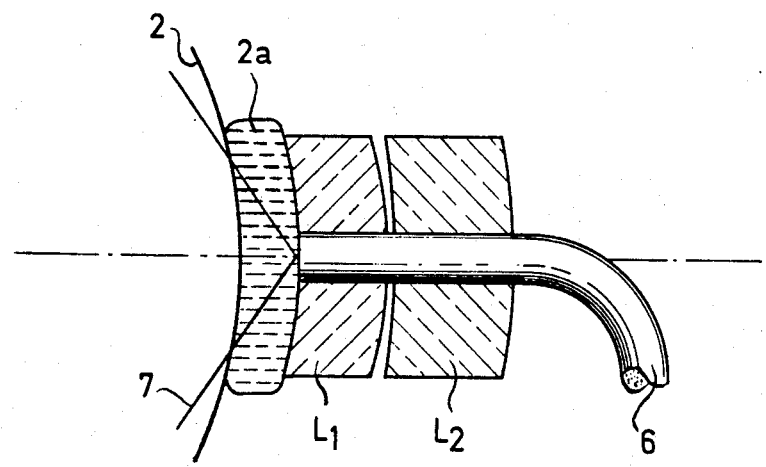
FIG. 2 is a similar view of the first lens group of an optical system in accordance with a second embodiment of the invention, provided with a light pipe for illumination of the fundus being examined.

In a second embodiment of the invention, the second lens group may be the same as in the first embodiment, but the first lens group is somewhat different, as illustrated in FIG. 2. In this embodiment, the lenses $L_1$ and $L_2$ of the first group are provided with a central borehole through which a light pipe 6 is extended. The cone of light 7 issues from the end of the light pipe 6, enters the eye of the patient through the intervening liquid body 2a and through the cornea 2, and illuminates the interior of the eye.

The data for the preferred dimensioning of the lenses in accordance with the invention are given in the following table. The symbols in the table have the usual meanings customary in lens patents, the individual lens elements being numbered consecutively from front to rear, each lens L being identified by a separate numerical subscript. Thicknesses and spacings are numbered in a single numerical sequence from front to rear, and are indicated by d with a numerical subscript. The focal length of the Fresnel lenses is indicated at f. Linear dimensions are expressed in millimeters. The index of refraction $n_d$ and the Abbe number $v_d$ are shown, the latter with respect to a convenient wavelength such as 5876 A. The notation will be clear to those skilled in the art, especially when comparing the table with FIG. 1.

| Lens | Radii | Vertex thicknesses and spacings | $n_d$ | $v_d$ |
|---|---|---|---|---|
| $L_1$ | $R_1 = 7,8298$ mm | $d_1 = 1,50$ mm | 1.52249 | 59.48 |
|  | $R_1' = 6,9783$ mm | $d_2 = 0,05$ mm |  |  |
| $L_2$ | $R_2 = 12,785$ mm | $d_3 = 2,00$ mm | 1.73350 | 51.65 |
|  | $R_2' = 10,100$ mm | $d_4 = 21,8$ mm |  |  |
|  |  | $d_5 = 0,1$ mm |  |  |
|  |  | $d_6 = 7$ mm |  |  |
| $L_3$ | (Fresnel) f = 55 mm |  |  |  |
| $L_4$ |  |  |  |  |

What is claimed is:

1. An optical system for forming an image of the retina of an eye, comprising a first lens group and a second lens group, the two groups cooperating with each other to form the image, the first lens group being substantially in contact with the eye to be examined through an interposed liquid film, the second lens group being separated from the first group by an air space and being dimensioned to conjugate the pupil of the eye being examined with the pupil of the eye of the observer, wherein the lenses of the first group and the second group have substantially the characteristics and relationship to each other indicated by the data in the following table, in which individual lenses are indicated by L with a numerical subscript corresponding to the consecutive number of the lens as numbered from front to rear, the radii of curvature of the front and rear surface of each lens are indicated by R and R', respectively, with a numerical subscript corresponding to the number of the lens, the vertex thicknesses of lenses and spaces between lenses are indicated by d with a numerical subscript corresponding to the numbering of the thicknesses and spacings in a single numerical series, the focal length of the Fresnel lenses $L_3$ and $L_4$ is indicated by f, all linear dimensions being expressed in millimeters, the index of refraction of certain of the lenses is given in the column headed $n_d$, and the index of dispersion or Abbe number of certain of the lenses, expressed with respect to the yellow d-line of the helium spectrum with a wavelength of 5876 Angstrom units, is given in the column headed $v_d$:

| Lens | Radii | Vertex thicknesses and spacings | $n_d$ | $v_d$ |
| --- | --- | --- | --- | --- |
| $L_1$ | $R_1 = 7,8298$ mm | $d_1 = 1,50$ mm | 1.52249 | 59.48 |
|  | $R_1' = 6,9783$ mm | $d_2 = 0,05$ mm |  |  |
| $L_2$ | $R_2 = 12,785$ mm | $d_3 = 2,00$ mm | 1.73350 | 51.65 |
|  | $R_2' = 10,100$ mm | $d_4 = 21,8$ mm |  |  |
|  |  | $d_5 = 0,1$ mm |  |  |
| $L_3$ |  | $d_6 = 7$ mm |  |  |
| $L_4$ | (Fresnel) $f = 55$ mm |  |  |  |

\* \* \* \* \*